(12) United States Patent
Chachques et al.

(10) Patent No.: US 7,341,062 B2
(45) Date of Patent: Mar. 11, 2008

(54) METHOD OF PROVIDING A DYNAMIC CELLULAR CARDIAC SUPPORT

(75) Inventors: Juan C. Chachques, Paris (FR); Howard J. Leonhardt, Weston, FL (US)

(73) Assignee: Bioheart, Inc., Sunrise, FL (US)

( * ) Notice: Subject to any disclaimer, the term of this patent is extended or adjusted under 35 U.S.C. 154(b) by 0 days.

(21) Appl. No.: 10/847,240

(22) Filed: May 17, 2004

(65) Prior Publication Data

US 2005/0002912 A1 Jan. 6, 2005

Related U.S. Application Data

(63) Continuation-in-part of application No. 10/095,630, filed on Mar. 11, 2002, now abandoned.

(60) Provisional application No. 60/274,990, filed on Mar. 12, 2001.

(51) Int. Cl.
*A61B 19/00* (2006.01)
(52) U.S. Cl. ...................................................... 128/898
(58) Field of Classification Search ................. 128/898
See application file for complete search history.

(56) References Cited

U.S. PATENT DOCUMENTS

| | | | |
|---|---|---|---|
| 4,735,205 A | | 4/1988 | Chachques et al. |
| 5,130,141 A | * | 7/1992 | Law et al. .................. 424/548 |
| 5,251,621 A | | 10/1993 | Collins |
| 5,602,301 A | | 2/1997 | Field |
| 6,110,459 A | | 8/2000 | Mickle et al. |
| 6,151,525 A | | 11/2000 | Soykan et al. |
| 2002/0124855 A1 | * | 9/2002 | Chachques .................. 128/898 |

OTHER PUBLICATIONS

Chachques et al., *Electrostimulation Enhanced Fatigue Resistant Myosin Expression in Cellular Cardiomyoplasty* 2001, Circulation, 104 (Suppl. 2):555-556 (Abstract No. 2626).
Yao et al. *Long-term Outcome of Fetal Cell Transplantation on Postinfarction Ventricular Remodeling and Function* (2003) Journal of Molecular and Cellular Cardiology, vol. 35, pp. 661-670.
Zimmermann et al., *Engineered Heart Tissue for Regeneration of Diseased Hearts*, (2004) Biomaterials vol. 25, pp. 1639-1647.
Shimizu et al., *Electrically Communicating Three-Dimensional Cardiac Tissue Mimic Fabricated by Layered Cultured Cardiomyocyte Sheets*, (2002) J Biomedical Materials Research vol. 60, pp. 110-117.
Pratt et al, *Synthetic Extracellular Matrices for In Situ Tissue Engineering*, Biotechnology and Bioengineering (2004) vol. 86, pp. 27-36.
Willey et al. *Focal Complex Formation in Adult Cardiomyocytes is Accompanied by the Activation of Beta3 Integrin and C-Src,*. (2003) Journal of Molecular Cellular Cardiology, vol. 35, pp. 671-683.
Xiong, et al., *Integrins, Cations and Ligands: Making the Connection*, (2003) Journal of Thrombosis and Haemostasis vol. 1, pp. 1642-1654.

* cited by examiner

*Primary Examiner*—William H. Matthews
(74) *Attorney, Agent, or Firm*—Hodgson Russ LLP

(57) ABSTRACT

The present invention provides a method for repairing damaged myocardium. The method comprises using a combination of cellular cardiomyoplasty and electrostimulation for myogenic predifferentiation of stem cells and to synchronize the contractions of the transplanted cells with the cardiac cells. The method comprises the steps of obtaining stem or myogenic cells from a donor, culturing and electrostimulating the isolated cells in vitro, and implanting the cells into the damaged myocardium.

8 Claims, No Drawings

METHOD OF PROVIDING A DYNAMIC CELLULAR CARDIAC SUPPORT

This application is a Continuation In Part of U.S. patent application Ser. No. 10/095,630, filed Mar. 11, 2002, now abandoned which claims the priority of U.S. Provisional Application Ser. No. 60/274,990, filed on Mar. 12, 2001, the disclosures of which are incorporated herein by reference.

FIELD OF THE INVENTION

The present invention relates generally to the field of myocardial repair and more particularly to a method for the repair of damaged myocardium by a combination of cellular based therapy and electrostimulation.

BACKGROUND OF THE INVENTION

Heart failure is a significant public health problem in contemporary cardiology. Heart failure, estimated to occur in 1% to 4% of the population, increases exponentially with age, so that current demographic trends in industrialized nations predict a dramatic increase in the number of patients with heart failure during coming decades as the populations of these countries grow older.

Heart failure is associated with significant morbidity, high incidence of complications, frequent hospitalization and rising healthcare costs. In the United States alone, an estimated 5 million individuals have a diagnosis of "congestive heart failure", and an additional 400,000-500,000 new cases are diagnosed annually.

Due to the restricted number of heart donors for heart transplantation and the high cost and drawbacks of mechanical assist devices, a large proportion of end stage heart failure patients need therapies other than current standard modalities. Approximately 25% of patients on waiting lists for heart transplantation die due to limited donor heart availability and more than 50% of all such patients succumb within 5 years of initial diagnosis.

Congestive cardiac failure is caused by a decrease in myocardial contractility due to mechanical overload or by an initial defect in the myocardial fiber. The alteration in diastolic function is inextricably linked with the pathophysiology of cardiac insufficiency. Despite a widely varying and diverse etiology of congestive cardiac failure (e.g. ischemic or idiopathic dilated cardiomyopathies), the pathophysiology is to a great extent constant with the alteration of myocardial contractility as the predominant factor. This contractility defect causes an elevation of the ventricular wall tension resulting in a progressive decline in the contractility of the myocardial fibers. A less-efficient, weakened heart must work harder to pump blood to the body and brain.

In addition to reduced myocardium contractility in combination with enlarged ventricular cavities, heart failure also involves in many cases defects of the heart conduction system resulting in either pump failure or arrhythmia. Approximately one-third of individuals with New York Heart Association (NYHA) Functional Class III/IV heart failure exhibit asynchronous heart rhythm. Further, electrical dyssynchronization between chambers (left or right bundle-branch block) are often found in the heart failure population. Recent studies aimed at correcting these conduction defects by right atrial/left ventricular or right atrial/biventricular pacing have shown beneficial clinical effects of these pacing modalities. Thus, such multisite cardiac pacing to restore appropriate timing between cardiac chambers activities is becoming a valid therapeutic alternative for heart failure patients. However, many patients (up to 40%) experience refractory heart failure due to a persistent myocardial dysfunction one or two years following the initiation of multisite pacing.

The cellular basis for congestive heart failure is based upon a lack of stem cells in the myocardium and the consequent inability of damaged heart cells to undergo repair or divide. Cellular cardiomyoplasty, i.e., transplantation of cells, instead of an entire organ, has a number of attractive attributes and is dependent on an ever expanding understanding of the molecular basis of skeletal myogenesis.

Cellular cardiomyoplasty procedures generally consist of transplanting myogenic cells into the damaged myocardium. Cardiomyoplasty utilizes myogenic cells such as cultured satellite cells (myoblasts), originating from a skeletal muscle biopsy of leg or arms of the same individual into whom the cells are transplanted. Satellite cells are mononucleated cells situated between the sarcolemma and the basal lamina of differentiated muscle fibers. They are thought to be responsible for postnatal growth, muscle fiber repair and regeneration. Another approach for cellular cardiomyoplasty consists of the utilization of bone marrow stem cells, autologous or fetal cardiomyocytes, or smooth muscle cells. However, one of the problems limiting the benefits of cellular cardiomyoplasty is that, even if the myoblasts survive after implantation, they often do not contract spontaneously and hence, they do not improve regional myocardial contractility. Further, the efficiency of cell transplantation engraftment and cellular organization in functional contractile units is often very poor since an efficient electrical coupling with adjacent viable cardiac tissue is difficult to achieve. Thus, there is a need to provide a method for inducing cells to contract spontaneously in order to enhance the contractility of the region into which they are implanted. Electrical activation of skeletal muscle has important clinical applications used in the treatment of a variety of disorders. In cardiology, functional electrostimulation of skeletal muscles has been used to assist ventricular function by way of surgical procedures which generally involve the use of autologous muscle in the form of a latissimus dorsi muscle flap wrapped around the ventricles and electrostimulated in a rhythmic fashion during systole. The success of this operation is due to physiological adaptation of skeletal muscle induced by chronic muscular electrostimulation enabling it to perform cardiac work ("myocardisation" of the latissimus dorsi muscle). Biochemically, there is a metabolic transformation of rapid muscular fibers with glycolytic metabolism, into slow fibers with oxidative metabolism resistant to fatigue. However, such myodardisation is incomplete and the technique remains a largely ineffective mechanism for compensating for damaged myocardium. Thus, there is a need for an effective method for repairing damaged myocardium that results in functioning myocardial cells in the damaged region.

SUMMARY OF THE INVENTION

The present invention provides a method for repairing damaged myocardium. The method comprises using a combination of cellular cardiomyoplasty and electrostimulation.

The method comprises the steps of obtaining myogenic cells obtained from a suitable source, culturing the myogenic cells in vitro and implanting them into the damaged myocardium. Following implantation, electrical stimulation in the form of atrial-biventricular resynchronization using multisite cardiac pacing is applied to facilitate synchronization of the transplanted cells with the myocardial cells.

DETAILED DESCRIPTION OF THE INVENTION

The present invention provides a method of repairing damaged myocardium by using a combination of electrical stimulation and cell transplantation. The method comprises the steps of isolating myogenic cells from a suitable source, culturing the myogenic cells in vitro, implanting the cells into damaged myocardium and providing electrostimulation to induce the implanted cells to contract in synchrony with the surrounding tissue. In a preferred embodiment, the cells are electrostimulated in vitro before being implanted.

For the present invention, myogenic cells can be obtained from any suitable source. Myogenic cells may be any type of cell capable of differentiating into a contractile cell, including skeletal myoblasts, satellite cells, bone marrow stromal cells, peripheral blood stem cells, post natal marrow mesodermal progenitor cells, smooth muscle cells, adult cardiomyocytes, fetal cardiomyocytes, neonatal cardiomyocytes, embryonic stem cells, bone marrow derived angioblasts, endothelial progenitor cells, CD34+ cells, CD133+ cells, CD117+ cells, bone marrow stromal cells or combinations thereof. The myogenic cells selected for transplantation should be able to differentiate into muscle cells either before or following implantation into the damaged myocardium. In a preferred embodiment, the cells are autologous to reduce the immune response. Thus, in the case of in vitro stimulation and implantation of autologous myogenic cells, the cells are obtained from an individual, cultured, stimulated in vitro, and implanted back into the myocardium of the same individual. If the cells are from a non-autologous source, following in vitro stimulation and implantation, immunosuppressants may be administered to the implantation recipient.

Myogenic cells can be isolated from a suitable source by methods well known to those skilled in the art. For example, the myogenic cells can be prepared by obtaining a biopsy from muscle tissue. The muscle can be any muscle tissue. The myogenic cells can be isolated from the biopsy by mincing and digesting the biopsied muscle tissue in a digestion solution containing enzymes such as trypsin and/or collagenase in phosphate buffered saline (PBS), and separating the myogenic cells using techniques well known to those skilled in the art. The cells may then be placed in culture immediately or kept in a suitable medium, such as Hank's Balanced Salt Solution, until cell culturing is started.

The myogenic cells may be cultured according to methods known to those skilled in the art. For example, the cells can be added to culture medium which may additionally comprise growth factors, serum, antibiotics or any of a variety of cell culture components known to those skilled in the art. The myogenic cells may then be allowed to remain in culture for various lengths of time and population doublings according to well known methods for culturing myogenic cells.

The myogenic cells according to the method of the present invention can be electrostimulated in culture prior to implantation. The electrostimulation can be carried out, for example, in culture flasks or dishes. Known pacemakers can be used to effect the electrostimulation by submerging sterile cathodes and anodes into culture flasks. Electrostimulation can then be carried out using bipolar pulses. An example of suitable ectrosimulation is a pulse amplitude of 5 Volts, a pulse width of 0.5 milliseconds at a rate of 120 pulses per minute. Such electrostimulation can be delivered over a period of hours to weeks until the cells are harvested for myocardial implantation and is different from, for example, from the type of electrostimulation provided for electroporation which was found to result in cell death for over 80% of cells in our experiments.

In another embodiment of the present invention, prior to electrostimulation the myogenic cells can be seeded into a three-dimensional (3D), biodegradable matrix that can support cell survival and promote cellular organization and then electrostimulated in the 3D matrix. The cells can be seeded in the matrix using known rotary cell culture systems. The matrix stimulates cells to influence differentiation and the cells actively remodel the matrix via local proteolytic activity. In this way, the use of electrostimulation of cells seeded in 3D biodegradable matrix allows the development of a bioengineered myocardium that can be used to repair congenital defects or to replace or repair large infarct or dyskinetic areas. Suitable 3D matrices can include, but are not limited to polymers, and cellular solids such as foam-like materials. The matrices used in the present invention are also preferably biodegradable, such as collagen type I and/or vitronectin. Additional examples of polymers suitable for use in the present invention include, but are not limited to, conducting polymers, non-conducting polymers, piezoelectric polymers, semiconducting polymers, insulators, and substituted ionomer resins (ionons). The polymers of the present invention may be conductive, as for example, polypyrrole, or may alternatively be a polymer having a backbone substituted with electroactive moieties such as heme, porphyryn, or ferrocene. For example, ionomer resin, a copolymer of ethylene and a vinyl monomer with an acid group, contains positively and negatively charged groups suitable for substitution of other electroactive moieties. Other polymers that are suitable in the practice of the present invention and include, but are not limited to, poly(p-phenylene), poly(p-phenylene-vinylene), poly(thiophene), and poly(aniline).

Electrostimulation of cells seeded in a 3D biodegradable matrix promotes angiogensis in vitro and in vivo induces an antiapoptotic effect on seeded cells which was confirmed in vitro by electronic microscopy. In addition, some integrins are expressed by cardiomyocytes and myoblasts and are involved in the myofibrillar organizations and mechanical coupling of the extracellular matrix with the myofibres. The expression of these integrins should be improved by the mechanical effects of electrostimulation. (See refs 25, 26, 27).

Autologous skeletal or smooth myoblasts, bone marrow stem cells, and/or cardiomyocytes obtained from a percutaneous right ventricular biopsy can be seeded in 3D bioengineered matrix (slowly biodegrable) and electrostimulated in vitro during 2 to 3 weeks, using a bipolar system including two leads provided with electrode surface area which can be varied at the time of the implantation in different matrix sizes (e.g. the leads described in U.S. Pat. No. 4,735,205, Apr. 5, 1988). In one embodiment, the matrix is a biological collagen type I+/-fibronectin matrix, in the form of a pre-moulded gel, incorporating RGD (Arg-Gly-Asp) motive to promote angiogenesis. Each coiled wire conductor is positioned at the opposite borders of the matrix, and immersed in the cell culture medium. A bipolar pulse generator delivering single pulses with a frequency from 30 to 140 pulse per minute with pulse amplitude from 2 to 7 volts and pulse width from 0.2 to 1.5 ms is connected to the leads.

After 2 to 3 weeks of in vitro electrostimulation, the matrix can be implanted into the infarcted scar or the pathological myocardium using a classic or minimally invasive surgical approach. The cellularized matrix can be implanted alone or in combination with intramyocardial implantation of cells or angiogenic and/or myogenic growth factors. In one embodiment, epicardial electrodes are implanted to facilitate postoperative long-term electrostimulation for atrio-biventricular resynchronization.

In addition to implanting the entire cellular matrix as described above, myogenic cells can be prepared for implantation from culture by a variety of methods known to those skilled in the art. Methods for expanding and purifying various cell types are well known to those skilled in the art. For example, details of such methods can be obtained from U.S. Pat. Nos. 5,130,141, 6,110,459, and 5,602,301. For example, cell culture flasks can be washed with PBS and the cells detached by using a trypsin solution. The contents of the culture flasks can be pelleted, the supernatant removed and replaced with PBS. The cell concentration and viability can be determined by a variety of well known methods, such as by Trypan blue assay using a cytometer. Thereafter, an appropriate number of cells can be centrifuged and resuspended in a suitable medium for transplantation. The in vitro stimulated myogenic cells are then implanted into the damaged myocardium. The myogenic cells may be supplemented with various growth factors including, but not limited to, vascular endothelial growth factors (VEGF) or fibroblast growth factors (FGFs).

Implantation of the myogenic cells can be accomplished by standard techniques such as via a catheter, direct injection, classic or minimally invasive thoroscopic surgical techniques known to those skilled in the art. The myogenic cell compositions may comprise cells in suitable implantation solutions, cells in combination with a porous carrier or other implantation components known to those skilled in the art, or in a three-dimensional biodegradable matrix according to the present invention.

After in vitro stimulation and implantation, the transplanted myogenic cells are paced in synchrony with the cardiac cycle by electrostimulation. Standard pacemakers including the new generation of 3-chamber pacemakers can be used in this process. In many cases, these pulse generators have already been implanted clinically in patients and therefore are known to be safe without substantial risk of induction of malignant ventricular arrythmias or ventricular fibrillation. Although not intending to be bound by any particular theory, it is considered that electrical stimulation induces predominant expression of slow fatigue resistant myosin (Chachques et al., 2001, Circulation, 104 (Suppl. 2):555-556, incorporated herein by reference). Post-implantation pacing requires sufficient voltage to activate all or most of the transplanted myoblasts. An example of a suitable range of pulse amplitude is from 2.5 to 7 volts. An example of a suitable range for pulse width is from 0.2 to 1.5 msec. In a preferred embodiment, the pulse amplitude is 5 V and the pulse width is 0.5 msec.

In one embodiment of post-implantation pacing, 3 electrodes can be implanted for cell pacing and cardiac resynchronisation. The placement of the three electrodes is: 1- Endocardial right atrium electrode; 2- Endocardial right ventricle electrode; 3- Left ventricular electrode. The electrodes are placed into a cardiac vein via the coronary sinus. Chronic atrial synchronized biventricular pacing is performed starting immediately after surgery using a three-chamber cardiac pacemaker. Ventricular channels are programmed using a minimum pulse amplitude of 5 Volts and a pulse width of 0.5 milliseconds. In cases of anatomical vein difficulty, a platinum-iridium epicardial pacing lead can be implanted in the left ventricular wall during cell implantation.

It will be recognized by those skilled in the art that while exemplary values are provided herein, other values can be determined by those skilled in the art by standard techniques.

EXAMPLE 1

This embodiment describes the isolation of skeletal myoblasts. A 1 $cm^3$ skeletal muscle piece (6-8 grams) was explanted from the patient's leg or arm, under sterile conditions. The biopsy was kept in Hank's Balanced Salt Solution (Gibco) at 4° C. until cell culturing is started. The operative wound was then closed. The explanted skeletal muscle pieces were washed in phosphate buffered saline (PBS, Gibco). In a Petri dish, adipose tissue and fascia were removed and the muscle was minced with scissors. The muscle fragments were washed in PBS until the supernatant remained clear. Centrifugation (Sigma 3K10, Bioblock) was carried out at 300 g for 5 minutes. The PBS was replaced with 20 mL of 0.25% trypsin-EDTA (Gibco) and placed in a 37° C. shaking waterbath. After 40 minutes the fragments were forced through a 10 mL disposable pipette. Following aspiration, cells were filtered through a 40 micrometer sieve (cell strainer nylon, Falcon, Becton Dickinson). The remaining muscle fragments on the filter were again subjected to enzymatic and mechanical digestion.

One mL of fetal calf serum (Gibco) was added to the filtrate and the solution was centrifuged at 300 g for 20 minutes. The resulting cell pellets were pooled in 10 ml fresh complete culture medium: 79% Ham-F12 medium, 25 pg/ml bFGF (human recombinant, Sigma), 20% Fetal Calf Serum, 1% penicillin/streptomycin (Gibco) and plated in a 100 mm Petri dish or cell culture flasks. Cell cultures were incubated at 37° C. in a humidified atmosphere containing 5% $CO_2$. Passaging of the cultures (1:5 split) was carried out at subconfluency to avoid the occurrence of myogenic differentiation at higher densities. During the first passage, preplating was applied to remove fibroblasts which attach quicker than satellite cells. The satellite cells are implanted upon the third passage.

The number of satellite cells in the primary culture was determined using immunofluorescence with a desmin primary antibody (1:20 Sigma) followed by FluoroLink™ Cy™3 (1:200, Amersham Pharmacia Biotech) as a second antibody.

EXAMPLE 2

This Example demonstrates the effects of conditioning myogenic cells with electrostimulation in vitro before myocardial implantation.

In one embodiment, the in vitro electrostimulation technique can be carried out in culture flasks/dishes. For example, single chamber bipolar pacemakers and 2 temporary cardiac leads (having a platinum-iridium alloy in the electrode surface) for each culture flask, can be used to electrostimulate the cell culture, medium and cells. Both sterile electrodes (cathode and anode) can be submerged separated into the flasks. Chronic electrostimulation can be started, for example, 7 days after cell seeding. Electrostimulation can be performed with a pulse frequency of from about 30 to 140 pulses per minute with a pulse amplitude of from about 2 to 9 Volts and a pulse width from about 0.2 to 1.5 ms. In a preferred embodiment, a 9 volt generator provides at 0.54 ms pulses to yield 120 pulses per minute to result in electrical impedance of about 832+/−24 Ohms. Single bipolar pulses with a pulse amplitude of 5 Volts, pulse width of 0.5 milliseconds, at a rate of 120 pulses per minute are delivered and stimulation lasts for up about 14 days until the cells are harvested for myocardial implantation. During the cell culture process, sequential passages are performed in order to obtain the final cell quantity. At each passage the cell suspension is split into, for example, 5 other flasks. After 3 weeks, more than 200 million cells can be obtained. Two electrodes are used for each tissue culture flask of 300 $cm^2$, and one pacemaker can be coupled to 10 electrodes using special connectors. Pacing the cell cultures at approximately 120 beats per minute is intended to imitate fetal heart rate in order to physiologically promote myogenic cell differentiation.

In a specific embodiment, two human cells types, CD34+ and bone marrow stromal cells were utilized. Eight patients with coronary disease and indication for coronary artery bypass graft (CABG) were selected. Four ml of bone marrow were collected after stemotomy. After selection using micro-magnetic immunobeads and the AutoMACS magnetic cell separation device (Miltenyi Biotec, Germany) to separate CD34+ cells from the mass of mononuclear bone marrow cells and purification, the cell cultures were electrostimulated during 3 weeks using two epicardial electrodes connected to a pulse generator delivering 9 Volts, 0.54 ms pulses (120 pulses per minute (ppm), similar to fetal cardiac frequency).

The impedances of the cultures was 832+/−24 Ohms, similar to skeletal and heart muscles. The impedance was measured using the Medtronic A-V analyzer system (model 5311B), connected to both pacing electrodes. The electrostimulation over the CD34+ cells and stromal cells cultures showed myogenic morphologic modifications and immunologics with positive anti-desmin anti-troponin results. Cell division was increased in the electrostimulated cultures. In vitro quantification of cells was performed using flow cytometry. The degree of cell differentiation in the cell cultures was estimated with desmin and troponin I—C antibodies and demonstrated myogenic morphologies and increased cell division.

EXAMPLE 3

This Example demonstrates techniques for implantation of the in vitro stimulated cells. Before cell implantation, the growth medium of each culture was tested aerobically and anaerobically in broth for its sterility. The cell culture flasks (TPP, Trasadingen, Switzerland) containing from 1 to 20 million cells each were washed with PBS. Upon detachment of the cells using 2 mL trypsin-EDTA, 2 mL of complete culture medium were added to each cell suspension. The contents of the 100 culture flasks were pooled and spun at 300 g for 15 minutes. The supernatant was removed and replaced with 20 mL of PBS. The cell concentration and viability were determined with Trypan blue (Gibco) using a Malassez cytometer (Polylabo). The calculated volume of cell suspension containing 100 million cells (or more, up to 800 million cells) is transferred to a 50 mL tube and centrifuged at 300 g for 5 minutes. The final cell pellet was resuspended in 5 ml of complete culture medium and 0.5% human albumin.

The heart was exposed by minithoracotomy or stemotomy. The infarction site was identified. Satellite cells were then injected using a Hamilton syringe, by multiple injection points (10 to 20). The volume of implanted cells, the volume of injection and the number of injection points depend on the size and the configuration of the myocardial infarcted area. Injections can be epicardial using standard or minimally invasive thorascopic procedures, endoventricular using a catheter based cell delivery assisted by 3D electromechanical mapping bi-plane fluoroscopy and ultrasound guidance and/or with an MRI compatible catheter, or intravascular by catheter based intracoronary, intravenous, or systemic methods.

EXAMPLE 4

This Example demonstrates that electrical stimulation of implanted myogenic cells improves heart function. To illustrate this embodiment, the following groups were used. Group 1 (n=6): Infarction (control). Group 2 (n=6): Infarction +atrial synchronized biventricular pacing (BV) stimulation (control). Group 3 (n=5): Infarction +myoblast transplantation. Group 4 (n=5) Infarction+myoblast transplantation+BV. Groups 3 and 4 included 25 million cultured myoblasts (from femoral biceps muscle) labeled with DAPI (diamidino phenylidolo) and were injected in the infarcted area. In groups 2 and 4, BV was performed using epicardial electrodes. Serum troponin I levels were used to evaluate the infarction. Echocardiographic and immunohistological studies were performed at 2 months. Two sheep died after infarction. Serum troponin I rose to 126+/−70 ng/ml 2 days following infarction. Echocardiography showed a significant improvement in ejection fraction (47+/−vs 36+/−4%) and a limitation of LV dilation (49+/−7 vs 69+/−2 ml) in group 4 vs control group. Viable DAPI labeled cells were identified in the infarcted areas. Differentiation of myoblasts into myotubes was significantly improved in group 4. In this group, immunocytological studies showed enhanced expression of slow myosin heavy chain compared to other groups. These results demonstrate that electrostimulation enhanced expression of slow myosin heavy chain which is better adapted at performing cardiac work.

REFERENCES

1) Chachques et al. Progress in Artificial Organs, Cleveland, Ohio, 1986, ISAO Press, P 409-412.
2) Chachques et al. Ann NY Acad Sciences 1987, 494: 445-448.
3) Chachques et al. Circulation 1988, 78 (Suppl 3): 203-216.
4) Rajnoch et al. J Thorac Cardiovasc Surg 2001, 121: 871-878.
5) Salmons et al. Muscle & Nerve 1981; 4:94-105.
6) Salmons et al. J. Physiol. Lond. 1969, 210:535-549.
7) Salmons et al. Nature 1976; 263:30-34.
8) Pette et al. Pfluegers Arch 1973; 338:257-272.
9) Naumann et al. Differentiation 1994; 55:203-211.
10) Wehrle et al. Differentiation 1994; 58:37-46.
11) Pette et al. Rev Physiol Biochem Pharmacol 1992; 120:116-202.
12) Taylor et al. Nat Med 1998; 4:929-933.
13) Dorfman et al. J Thorac Cardiovasc Surg 1998; 116: 744-751.
14) Scorsin et al. J Thorac Cardiovasc Surg 2000; 119:1169-75.
15) Gras et al. Pace 1998; 21 (Pt.II):2249-2255.
16) Auricchio et al. Circulation 1999; 99:2993-3001.
17) Stellbrink et al., 2001, J. Am. Coll. Cardiol. 38:1957-65.
18) Orlic et al., 2001, Nature, 410:701-705.
19) Tomita et al., 1999, Circulation, 100:247-56.
20) Chachques JC, et al., Ann Thorac Surg 2004; 77:1121-30.

21) Chachques JC, et al., Circulation 2001; 104 (Suppl 2):555-556.
22) Chachques JC, et al., Herz 2002; 27:570-8.
23) Chachques JC, et al., J Card Surg 2002; 17:194-200.
24) Haider HK, et al., Mol Ther 2004; 9:14-23.
25) Pratt AB. et al.: Biotechnol Bioeng. 2004; 86:27-36.
26) Willey CD, et al., J Mol Cell Cardiol 2003; 35:671-83.
27) Xiong JP, et al., J Thromb Haemost 2003; 1:1642-54.

We claim:

1. A method for repairing the myocardium of an individual comprising the steps of:
   a. obtaining myogenic cells;
   b. culturing the myogenic cells in vitro;
   c. providing in vitro electrical stimulation to the myogenic cell culture to simulate fetal heart rate and synchronize contraction of the cells, wherein the electrical stimulation has a frequency of about 120 pulses per minute, a pulse amplitude of from 2.5-6 volts, and a pulse width of from 0.2-0.7 milliseconds; and
   d. implanting the electrically stimulated myogenic cells into the myocardium.

2. The method of claim 1 comprising the additional step of providing electrical stimulation to the implanted cells to induce the implanted cells to contract in synchrony with the surrounding tissue.

3. The method of claim 1, wherein the myogenic cells are selected from the group consisting of skeletal myoblasts, bone marrow stromal cells, peripheral blood stem cells, multipotent adult progenitor cells (MAPC), smooth muscle cells, adult cardiomyocytes, fetal cardiomyocytes, neonatal cardiomyocytes, embryonic stem cells, bone marrow derived angioblasts, endothelial cells, CD34+ cells, CD133+ cells, CD117+ cells and combinations thereof.

4. The method of claim 1, wherein the pulse has an amplitude of 5 volts and a width of 0.5 milliseconds.

5. The method of claim 1, wherein the myogenic cells cultured in vitro are cultured in a three-dimensional, biodegradable matrix.

6. The method of claim 2, wherein the electrical stimulation provided to the implanted cells is in the form of atrial synchronized biventricular pacing.

7. The method of claim 1, wherein the cells of step b. are cultured in a biodegradable matrix.

8. The method of claim 1, wherein the width is 0.5 milliseconds.

* * * * *